United States Patent
Rice et al.

(10) Patent No.: US 6,673,035 B1
(45) Date of Patent: Jan. 6, 2004

(54) MEDICAL INJECTOR AND MEDICAMENT LOADING SYSTEM FOR USE THEREWITH

(75) Inventors: Mark W. Rice, Minneapolis, MN (US); Paul R. Lesch, Jr., Lexington, MN (US); Sheldon J. Nelson, New Hope, MN (US); Timothy D. Byland, Savage, MN (US)

(73) Assignee: Antares Pharma, Inc., Minneapolis, MN (US)

( * ) Notice: Subject to any disclaimer, the term of this patent is extended or adjusted under 35 U.S.C. 154(b) by 0 days.

(21) Appl. No.: 09/692,487

(22) Filed: Oct. 20, 2000

Related U.S. Application Data
(60) Provisional application No. 60/160,893, filed on Oct. 22, 1999.

(51) Int. Cl.[7] .............................. A61M 5/30; A61M 5/20
(52) U.S. Cl. ......................................... 604/72; 604/135
(58) Field of Search ........................... 604/68, 72, 131, 604/136, 135, 133, 905, 69, 70, 71, 181, 187, 232

(56) References Cited

U.S. PATENT DOCUMENTS

| | | |
|---|---|---|
| 1,512,294 A | 10/1924 | Marcy |
| 1,687,323 A | 10/1928 | Cook |
| 2,354,649 A | 8/1944 | Bruckner .................... 128/218 |
| 2,607,344 A | 8/1952 | Brown ........................ 128/218 |
| 2,645,223 A | 7/1953 | Lawshe et al. ............. 128/173 |
| 2,648,334 A | 8/1953 | Brown et al. ............... 128/173 |
| 2,699,166 A | 1/1955 | Dickinson, Jr. et al. ..... 128/173 |
| 3,557,784 A | 1/1971 | Shields ....................... 128/173 |
| 3,770,026 A | 11/1973 | Isenberg ....................... 141/2 |
| 4,338,980 A | 7/1982 | Schwebel et al. ............. 141/18 |
| 4,936,833 A | 6/1990 | Sams ........................... 604/232 |
| 4,973,318 A | 11/1990 | Holm et al. ................. 604/208 |
| 5,226,895 A | 7/1993 | Harris ......................... 604/208 |
| 5,232,459 A | 8/1993 | Hjertman .................... 604/208 |
| 5,256,142 A | 10/1993 | Colavecchio ................ 604/68 |
| 5,279,585 A | 1/1994 | Balkwill ...................... 604/207 |
| 5,279,586 A | 1/1994 | Balkwill ...................... 604/207 |
| 5,281,198 A | 1/1994 | Haber et al. .................. 604/86 |
| 5,292,318 A | 3/1994 | Haber et al. ................ 604/407 |
| 5,308,341 A | 5/1994 | Chanoch ..................... 604/208 |
| 5,330,431 A | 7/1994 | Herskowitz ................. 604/153 |
| 5,542,760 A | 8/1996 | Chanoch et al. ............ 366/160 |
| 5,573,042 A | 11/1996 | De Haen ........................ 141/2 |
| 5,599,302 A * | 2/1997 | Lilley et al. ................. 604/135 |
| 5,649,912 A | 7/1997 | Peterson ...................... 604/187 |
| 5,658,259 A | 8/1997 | Pearson et al. ............. 604/232 |
| 5,688,251 A | 11/1997 | Chanoch ..................... 604/208 |
| 5,704,911 A | 1/1998 | Parsons ........................ 604/72 |
| 5,725,508 A | 3/1998 | Chanoch et al. ............ 604/207 |
| 5,769,138 A * | 6/1998 | Sadowski et al. ............. 141/25 |
| 5,788,670 A * | 8/1998 | Reinhard et al. ........... 604/191 |
| 5,827,232 A | 10/1998 | Chanoch et al. ............ 604/208 |
| 5,851,198 A | 12/1998 | Castellano et al. ........... 604/68 |
| 5,860,456 A | 1/1999 | Bydlon et al. ................ 141/25 |
| 5,873,857 A | 2/1999 | Kriesel ........................ 604/131 |
| 5,875,976 A * | 3/1999 | Nelson et al. ............... 239/329 |
| 5,879,327 A * | 3/1999 | Moreau DeFarges et al. .... 604/135 |
| 5,921,966 A | 7/1999 | Bendek et al. .............. 604/207 |
| 6,123,684 A * | 9/2000 | Deboer et al. .............. 604/134 |
| 6,309,371 B1 * | 10/2001 | Deboer et al. ................ 604/68 |

FOREIGN PATENT DOCUMENTS

WO     WO 99/10030     3/1999

\* cited by examiner

*Primary Examiner*—Manuel Mendez
*Assistant Examiner*—Mark K. Han
(74) *Attorney, Agent, or Firm*—Winston & Strawn LLP

(57) ABSTRACT

The present invention discloses a medical injector and medicament loading system for use therewith. The medicament loading system includes cap for a medicament cartridge. The cap has a post for causing movement of the cartridge stopper toward the seal when the cap engages the medicament cartridge to thereby eliminate adhesion between the medicament chamber and the stopper. The medical injector according to the present invention includes the medicament loading system, i.e. a cartridge assembly, a needle free syringe assembly, and a power pack assembly.

25 Claims, 11 Drawing Sheets

MEDICAL INJECTOR AND MEDICAMENT LOADING SYSTEM FOR USE THEREWITH

CROSS-REFERENCE TO RELATED APPLICATIONS

The benefit of Provisional Application No. 60/160,893 filed on Oct. 22, 1999 is claimed under 35 U.S.C. §119(e).

FIELD OF THE INVENTION

The present invention is directed to a device for delivery of medicament, and in particular to a compact jet injector and loading system used with standard medicament cartridges.

BACKGROUND OF THE INVENTION

A wide variety of needle free injectors are known in the art. Examples of such injectors include those described in U.S. Pat. No. 5,599,302 issued to Lilley et al., U.S. Pat. No. 5,062,830 to Dunlap, and U.S. Pat. No. 4,790,824 to Morrow et al. In general, these and similar injectors administer medication as a fine, high velocity jet delivered under sufficient pressure to enable the jet to pass through the skin.

Although these injectors are quite successful from a technical point-of-view in achieving the desired delivery of medicament, most commercially available needle free injectors have practical limitations. For example, most needle free injectors are bulky in size. In addition to the undesirable size, some needle free injectors require a complex sequence of coupling and uncoupling the injector to a vial containing the medicament. Thus, there is a perception by the user that the injector is difficult to use. Finally, some needle free injectors cannot be used with standard medicament cartridges, i.e. a cylindrical chamber, typically made of glass, having a first end with a seal penetrable by a needle to draw medicament out of the cartridge and a second end with a movable stopper.

Thus, there exists a need for an improved medical injector and loading system that is compact, usable with standard medicament cartridges, and perceived as easy to operate.

SUMMARY OF INVENTION

The present invention is directed to a cap for a medicament cartridge. The cartridge has a chamber containing medicament, a first end of the chamber having a seal, and a second end of the chamber having a stopper movable towards the seal as medicament is drawn out of the chamber. The cap according to the present invention comprises an interior portion for receiving the second end of the chamber and a post for causing movement of the stopper toward the seal when the cap engages the medicament cartridge to thereby eliminate adhesion between the chamber and the stopper.

The adhesion-eliminating cap can be used in combination with an adapter for transfer of medicament out of the cartridge. The action of the cap in conjunction with the adapter is to allow the purging of gas or air from the cartridge and thus assist in better dosage accuracy and injection quality. The adapter has a first side that mates with the first end of the chamber and has a needle for penetrating the seal upon insertion of the cartridge assembly in the adapter, a second side, and a wall between the first and second sides. The wall has an opening in fluid communication with the needle to create a pathway for medicament as medicament is drawn out of the chamber. Preferably, the first side of the adapter has a plurality of resilient tabs that flex outward upon insertion of the medicament cartridge into the adapter and flex inward after the seal is substantially flush with the wall for locking the medicament cartridge into the adapter.

In one embodiment, the cap and adapter are coupled with a housing. The housing has a first end connectable with the cap and a second end connectable with the adapter. The housing can include a window for visualization of at least a portion of the medicament cartridge.

The cap according to the present invention can be used with a wide variety of injection devices, including a needle free injector. Preferably, the needle free injector comprises a needle free syringe assembly and a power pack assembly. The needle free syringe assembly includes a nozzle member defining a fluid chamber and having a proximal end that mates with the second side of the adapter. The needle free syringe assembly also includes a plunger movable in the fluid chamber. The power pack assembly includes a housing having a proximal end connectable with the distal end of the nozzle member, a trigger assembly, and an energy source operatively associated with the trigger assembly. Movement of the trigger assembly activates the energy source to move the plunger in a first direction to expel medicament from the fluid chamber when the adapter is not connected to the needle free syringe assembly and movement of the plunger in a second direction draws medicament out of the cartridge chamber and into the fluid chamber when the adapter is connected to the needle free syringe assembly.

In one embodiment, the first end of the cartridge assembly housing has a female thread and the cap has a collar insertable into the first end of the cartridge housing. The collar is provided with a male thread that mates with the female thread for connection of the housing with the cap.

The present invention can be used with lyophilized medicament. Specifically, the medicament chamber has a first chamber containing a lyophilized medicament, a second chamber containing a reconstituting fluid, a dividing member separating the first and second chambers, and a bypass channel for providing fluid communication between the first and second chambers upon movement of the dividing member. Fluid pressure generated by movement of the stopper causes movement of the dividing member. The attached adapter assembly allows the venting of the gas or air from the first chamber thereby facilitating dividing member movement and fluid flow. This also allows minimizing the air or gas present in the reconstituted fluid prior to injection.

The present invention is also directed to a medical injector assembly comprising a cartridge assembly for holding a medicament cartridge and a syringe assembly. The medicament cartridge has a chamber containing medicament, a first end of the chamber with a seal, and a second end of the chamber with a stopper movable towards the seal as medicament is drawn out of the chamber. The cartridge assembly comprises a cap with an interior for receiving the second end of the chamber and an end having a post causing movement of the stopper toward the seal as the medicament cartridge is inserted in the cap to thereby eliminate adhesion between the chamber and the stopper. The syringe assembly comprises a fluid chamber, a needle, and a plunger. The plunger is movable in the fluid chamber so that movement in the first direction expels medicament from the fluid chamber. Movement of the plunger in the second direction draws medicament out of the cartridge chamber into the fluid chamber when the syringe assembly is in fluid communication with the medicament cartridge. In one embodiment describing such fluid communication, the needle on the syringe assembly penetrates the seal on the first end of cartridge chamber. Another embodiment anticipates a receiving member for the syringe needle in the adapter. The seal penetrating needle in this embodiment is integral to a first side of the adapter (the side that mates with the first end of the cartridge chamber). The second side of the adapter consists of a receiving member for the syringe and syringe needle designed as to allow fluid communication with the first side of the adapter.

DESCRIPTION OF THE PREFERRED EMBODIMENTS

Figure 1:
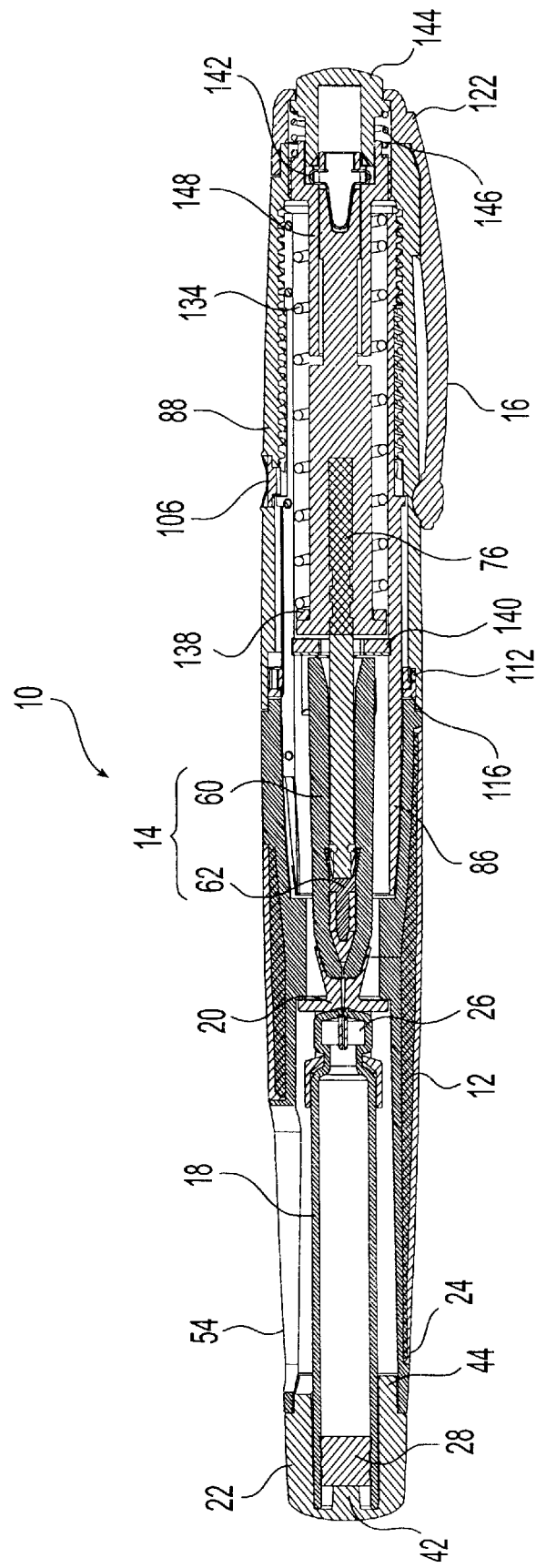
FIG. 1 is a cross-sectional view of a medical injector and medicament loading system (cartridge assembly) according to the present invention.
Figure 2:
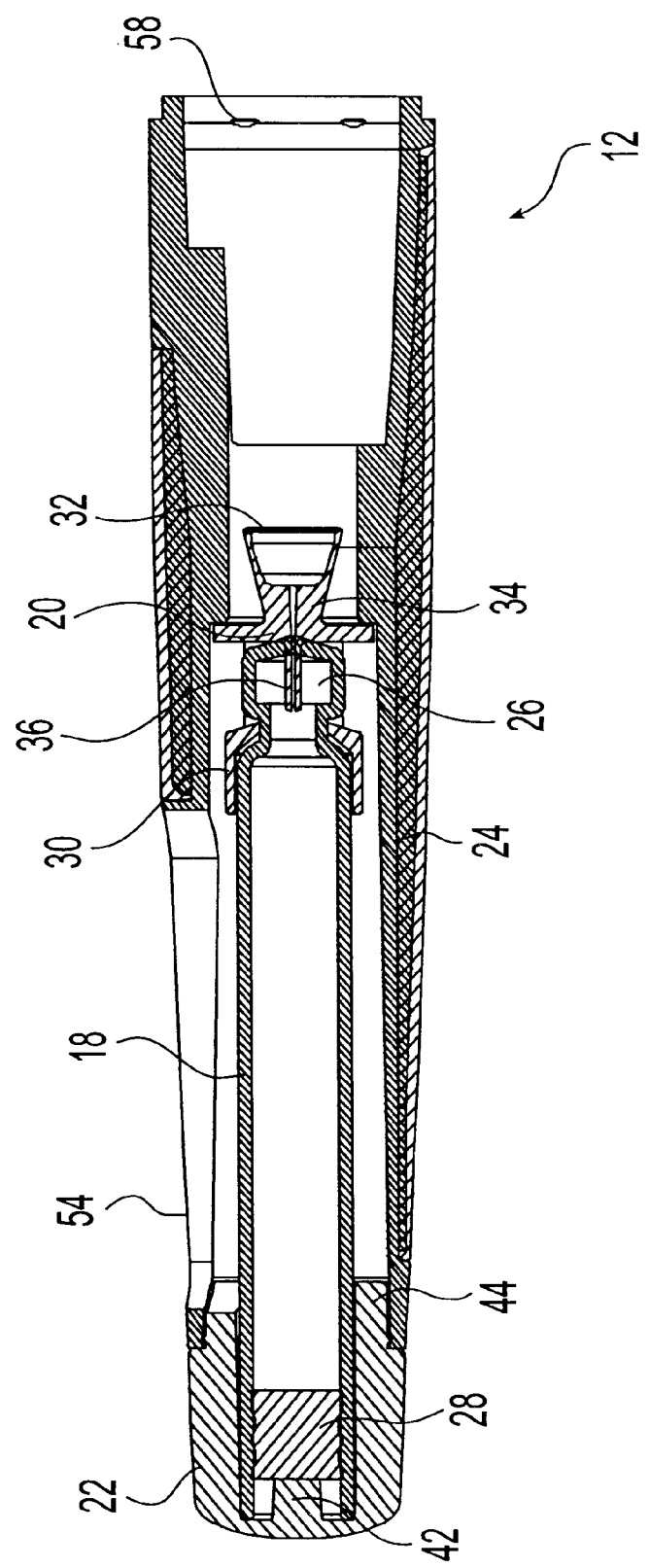
FIG. 2 is cross-sectional view of the cartridge assembly of FIG. 1 showing a cap, adapter, and a cartridge housing.

As shown in FIG. 1, a medical injector 10 according to the present invention comprises a medicament loading system or cartridge assembly 12, a needle free syringe assembly 14, and a power pack assembly 16. As best seen in FIGS. 1 and 2, cartridge assembly 12 includes a medicament cartridge 18 for holding medicament, an adapter 20 for transferring medicament from medicament cartridge 18 to needle free assembly 14, a cap 22 for holding medicament cartridge 18, and a cartridge housing 24. Because medicament cartridges are commercially sold in a variety of sizes, adapter 20, cap 22, and cartridge housing 24 are designed to be used with different sized medicament cartridges 18. Medicament cartridge 18 comes pre-filled with medicament and has seal 26 on one end and a stopper 28 on the other end, which moves towards seal 26 as medicament is drawn out.

Figure 3:
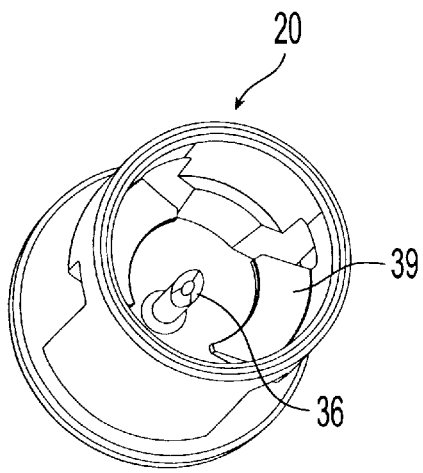
FIG. 3 is a perspective view of an adapter.
Figure 4:
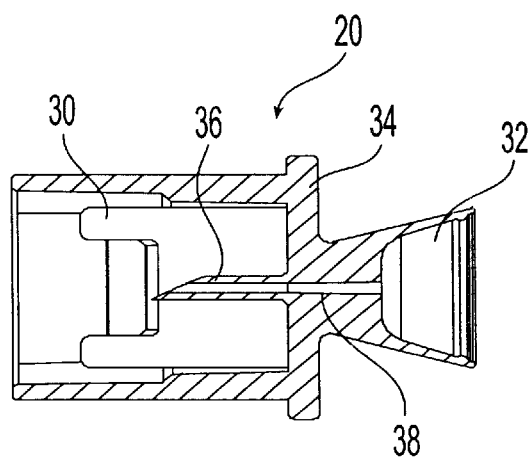
FIG. 4 is a cross-sectional view of the adapter of FIG. 3.

The first step in assembling cartridge assembly 12 is to couple medicament cartridge 18 with adapter 20. Adapter 20 has a first side 30 configured and dimensioned to mate with the end of medicament cartridge 18 that has seal 26 and a second side 32 configured and dimensioned to mate with needle free syringe assembly 14. Second side 32 can have a barrier with a so-called "zero diameter" hole or slit to minimize the potential for leakage and potential of contamination. As disclosed in U.S. Pat. No. 5,846,233, the disclosure of which is incorporated herein by reference, such a hole or slit only allows passage of fluid when stretched, i.e. when needle free syringe assembly 14 is mated to second side 32. FIGS. 3 and 4 show that first and second sides 30, 32 are separated by a wall 34. First side 30 includes a cartridge opening member, which is a needle 36 in the embodiment shown, for penetrating seal 26 and in fluid communication with a channel 38 so that a pathway for medicament to be drawn out of medicament cartridge 18 and into needle free syringe assembly 14 is formed. Needle 36 can be a metallic element, analogous to the needle on a conventional syringe, with a beveled end (single bevel, double bevel, tri-bevel, etc.) to facilitate penetrating seal 26. Alternatively, needle 36 can be a plastic spike. If needle 36 is a plastic spike, preferably it is made using an injection molding process so that needle 36 is integral to wall 34.

First side 30 also includes a frangible retaining member such as resilient tabs 39 that flex outward upon insertion of medicament cartridge 18 into adapter 20 and flex back inward after seal 26 is substantially flush with wall 34 to lock the medicament cartridge 18 into adapter 20. Because tabs 39 must be broken to remove medicament cartridge 18, tabs 39 help ensure that adapter 20 is disposed of after use and not reused with multiple medicament cartridges.

Figure 5:
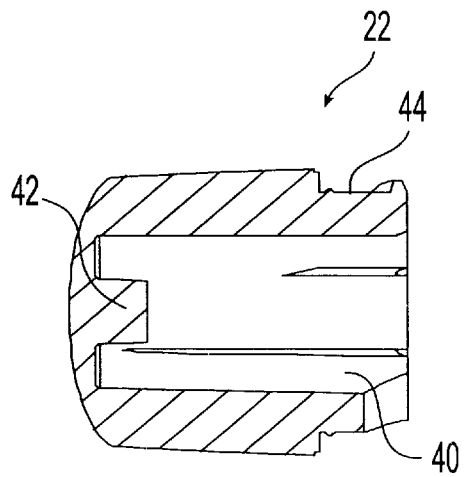
FIG. 5 is a cross-sectional view of a cap.

The next step in assembling cartridge assembly 12 is to attach cap 22 to medicament cartridge 18. As shown in FIG. 5, cap 22 has an interior 40 for receiving the end of medicament cartridge 18 that has stopper 28. As medicament cartridge 18 is inserted into interior 40, a post 42 slightly pushes stopper 28 toward seal 26. This serves two important functions. First, the slight movement of stopper 28 eliminates any adhesion between stopper 28 and medicament cartridge 18. Such adhesion occurs because medicament cartridge 18 is typically made of glass and stopper 28 is typically made of silicone rubber and adherence develops during storage of medicament cartridge 18. Elimination of the adhesion facilitates the drawing of medicament out of medicament cartridge 18. The slight movement of stopper 28 also purges air from medicament cartridge 18 to minimize introduction of air into needle free syringe assembly 14. As shown in FIG. 2, the movement of the post 42 to purge the air is insufficient to expel a substantial amount of the medicament from the chamber 64 with the seal opened by the opening member. In order to achieve the maximum purging effect, adapter 20 should be pointing upward when cap 22 is attached to medicament cartridge 18. Although cap 22 is preferably used in conjunction with adapter 20 and needle free assembly 14, cap 22 can be used with any medicament delivery device that relies on transfer of medicament from cartridge 18 into the device by drawing a vacuum through a needle that has penetrated seal 26. As shown in FIG. 2, the post 42 is in a post position with the cap 22 and cartridge housing 24 engaged, from which position movement of the post 42 past the post position towards the adapter 20 and first end of the cartridge 18 is prevented.

Figure 6:
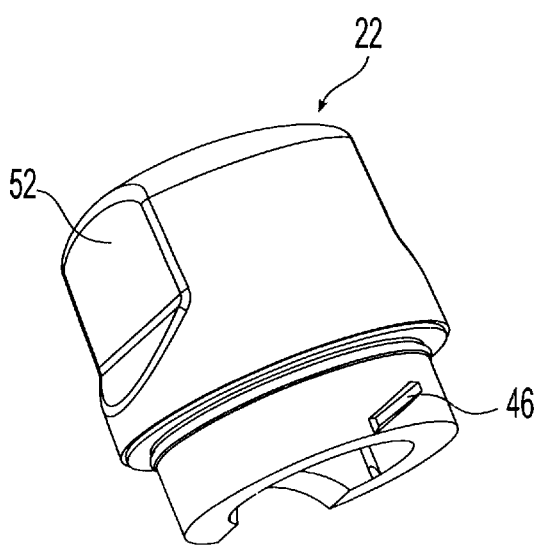
FIG. 6 is a perspective view of the cap of FIG. 5.
Figure 7:
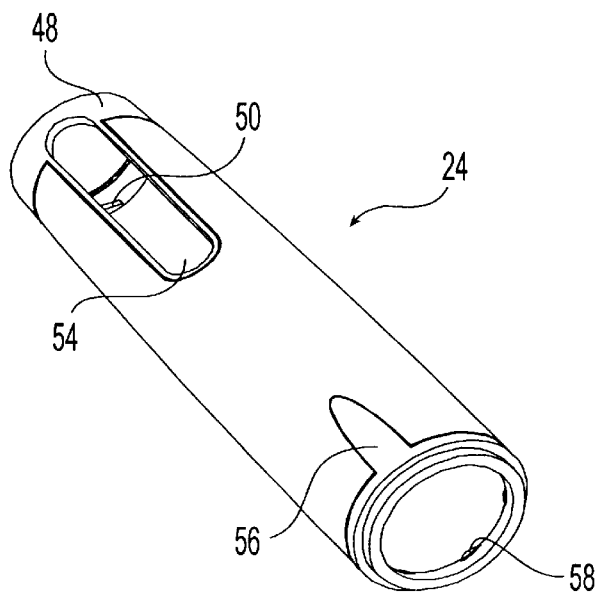
FIG. 7 is a perspective view of a cartridge housing.
Figure 8:
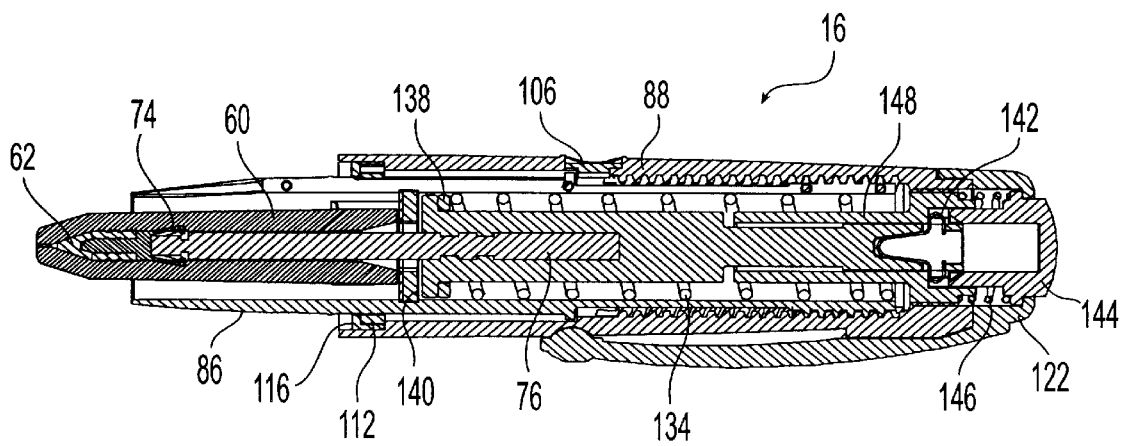
FIG. 8 is a cross-sectional view of the medical injector of FIG. 1 showing a power pack assembly and a needle free syringe assembly.
Figure 9:
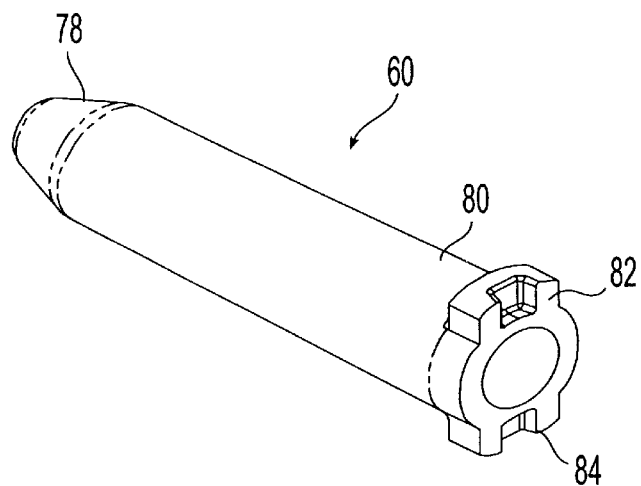
FIG. 9 is a perspective view of a nozzle member.
Figure 10:
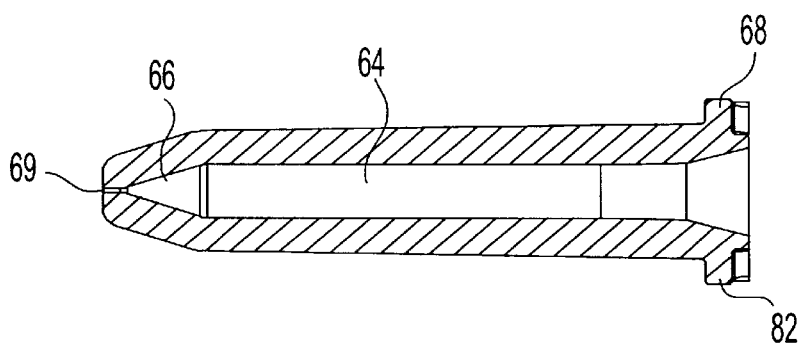
FIG. 10 is a cross-sectional view of the nozzle member of FIG. 9.
Figure 11:
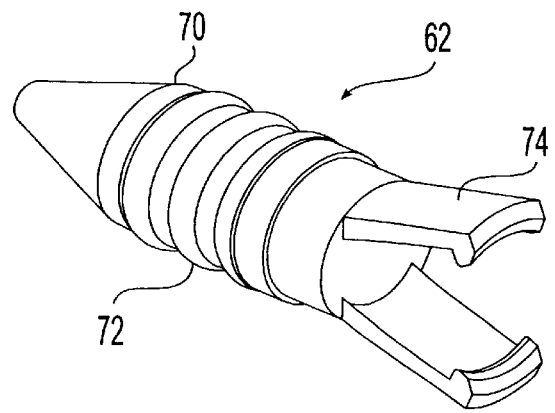
FIG. 11 is a perspective view of a plunger.

The final step in assembling cartridge assembly 12 is to connect cap 22 to cartridge housing 24. As shown in FIGS. 6 and 7, cap 22 has a collar 44 with a male thread 46 and a first end 48 of cartridge housing 24 has a female thread 50. Collar 44 inserts into first end 48 and male and female threads 46, 50 mate so that cap 22 is securely engaged and connected to cartridge housing 24 upon twisting, thus engaging the cap 22 and cartridge housing 24 in an engaged position and association for preventing movement of the cap 22 and post 42. As can be seen from the figures, positioning of the cartridge 18 in the cap 22 with respect to the post 42 and the positioning of the post in the positions of FIG. 1 causes the post 42 to move the stopper 28 to release adhesion therebetween. The exterior of cap 22 has flats 52 to facilitate handling. When assembled, a window 54 located on cartridge housing 24 provides a visual assurance of proper installation of medicament cartridge 18, the amount of medicament, and the location of stopper 28. As described in more detail below, markings 56 ensure alignment with power pack assembly 16 and ridges 58 mate with corresponding grooves on power pack assembly 16 to snap cartridge assembly 12 onto power pack assembly 16.

Prior to connecting cartridge assembly 12 and power pack assembly 16, needle free syringe assembly 14 must be attached to power pack assembly 16. FIGS. 1 and 8–11 show that needle free syringe assembly 14 includes a nozzle member 60 and a plunger 62. Nozzle member 60 includes a cylindrical fluid chamber 64 terminating at one end in a cone 66 and at the other end in an expanded area tail 68. Cone 66 can be a convex cone (as shown), a right circular cone, or any other suitable configuration. Cone 66 leads to an orifice 69 of a suitable diameter that would produce a jet stream of medicament under a given desired pressure range and depth of injection. Plunger 62 has a pressure wall 70 contoured to cone 66 and is positioned to slide within fluid chamber 64. Plunger 62 also includes a series of ridges 72 formed around its outer periphery to provide a seal and create a sterile boundary between the medicament and the outside of the nozzle member 60. As described in more detail below, legs 74 of plunger 62 compress around a ram 76 to operatively couple plunger 62 to ram 76. Legs 74 are resilient and ordinarily biased outward. However, the relative size of fluid chamber 64 keeps legs 74 compressed inward against ram 76 to maintain the coupling. When needle free syringe assembly 14 is removed from power pack assembly 16, legs 74 expand out into the expanded area of tail 68 so that plunger 62 remains with nozzle member 60. Thus, all of needle free assembly 14 can be disposed of after the prescribed number of injections.

A proximal end 78 of nozzle member 60 has a taper that matches that of adapter second side 32 so that when proximal end 78 is inserted into adapter second side 32, fluid chamber 64 is in fluid communication with needle 36 and channel 38 to allow transfer of medicament from medicament cartridge 18 into fluid chamber 64. A distal end 80 of nozzle member 60 has locking tabs 82 and each locking tab 82 is provided with a recess 84. Locking tabs 82 and recess 84 mate with corresponding features on power pack assembly 16 to lock needle free syringe assembly 12 to power pack assembly 16. These and other structural features of power pack assembly 16 will now be described.

Figure 12:
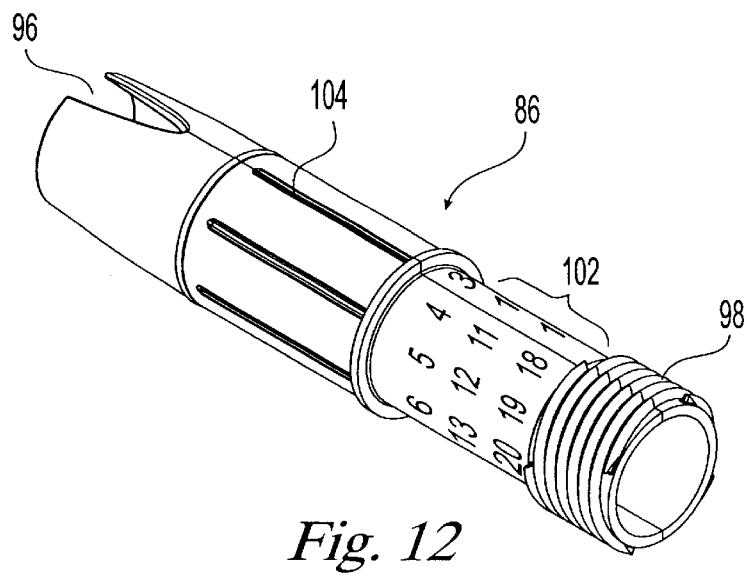
FIG. 12 is a perspective view of a proximal housing.
Figure 13:
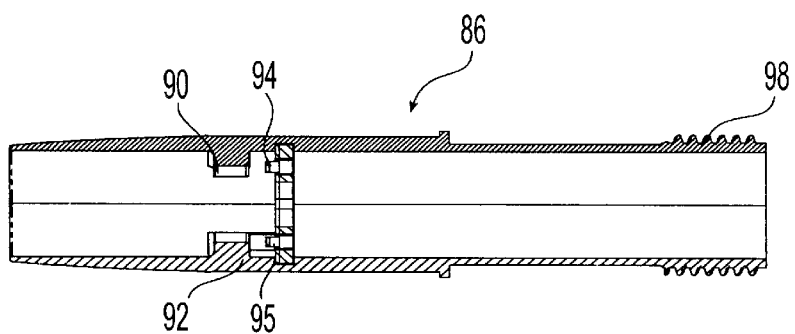
FIG. 13 is a cross-sectional view of the proximal housing of FIG. 12.
Figure 14:
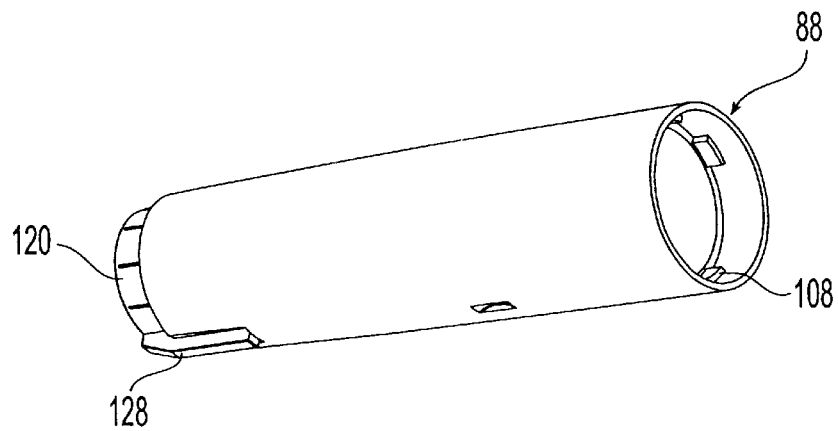
FIG. 14 is a perspective view of a distal housing.
Figure 15:
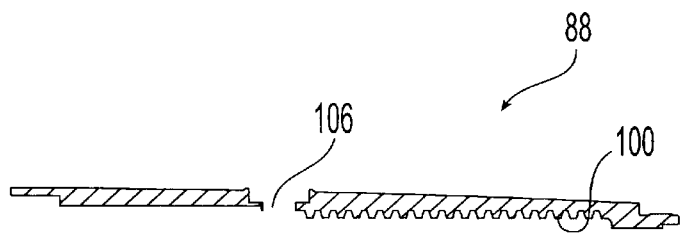
FIG. 15 is a cross-sectional view of the distal housing of FIG. 14.
Figure 15:
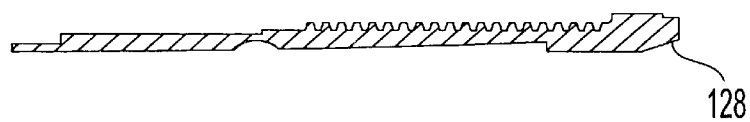

Power pack assembly 16 has a two part housing that includes a proximal housing 86 (FIGS. 12 and 13) and a distal housing 88 (FIGS. 14 and 15). Proximal housing 86 is a tube having a lumen. A portion of the lumen has a keyed surface 90 configured and dimensioned to receive nozzle member 60 of needle free syringe assembly 16. Keyed surface terminates in a ledge 92. In order to couple nozzle member 60 into proximal housing 86, nozzle member 60 is inserted into proximal housing 86 and twisted a quarter turn so that locking tabs 82 are resting against ledge 92. A resilient biasing member 94, having protrusions 95 that fit into recesses 84 of locking tabs 82, keeps nozzle member 60 biased against ledge 92.

The outer surface of proximal housing 86 is provided with cut outs 96, which are mirror images of markings 56 on cartridge housing 24 to ensure proper alignment of cartridge assembly 12 and power pack assembly 16. Cut outs 96 also function to allow viewing of medicament once it has been drawn into needle free syringe assembly 14. The outer surface of proximal housing 86 is also provided with threads 98 and the inner surface of distal housing 88 is provided with threads 100 so that when proximal housing 86 is inserted in distal housing 88, threads 98 mate with threads 100. As described in more detail below, the relative motion between proximal and distal housings 86, 88 allow arming and dosing of medical injector 10.

Figure 16:
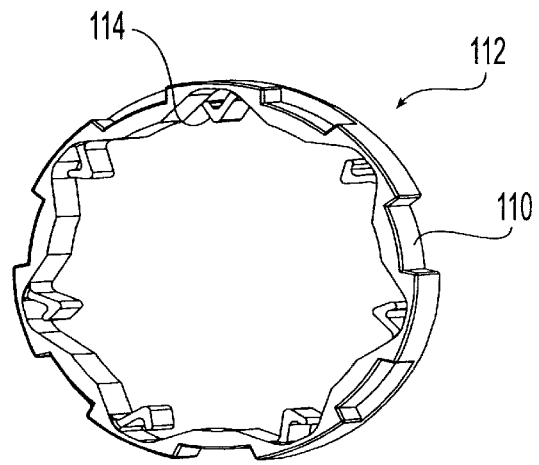
FIG. 16 is a perspective view of a dosage detent.
Figure 17:
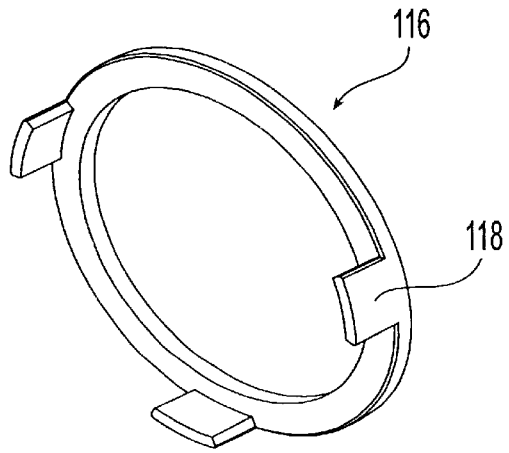
FIG. 17 is a perspective view of detent cover ring.

Indicia 102 on exterior of proximal housing 86 are for determining the dose of medicament to be injected and grooves 104 provide tactile and audible feedback of dosage of medicament. Specifically, only one of the numbers of indicia 102 is viewable through dosing window 106 located on distal housing 88. As distal housing 88 is rotated counter-clockwise relative to proximal housing 86, the number viewable in dosing window 106 increases to reflect a higher dose. A proximal end of distal housing 88 has protuberances 108 for receiving slots 110 of a dosing detent 112 (FIG. 16). Dosing detent 112 has a plurality of resilient detent forms 114. When distal housing 88 is slid over proximal housing 86, detent forms 114 are located over grooves 104 of proximal housing 86. As distal housing 88 is rotated relative to proximal housing 86, detent forms 114 flex into grooves 104 to create a physical stop at each unit of dosing. As dosing detent 112 would be visible and potentially subject to damage when cartridge assembly 12 is not connected to power pack assembly 14 (as viewed from the end), a detent cover ring 116 protects dosing detent 112. As shown in FIG. 17, detent cover ring 116 has pegs 118. These pegs 118 fit into those slots 110 of dosing detent 112 that are not used for protuberances 108.

Figure 18:
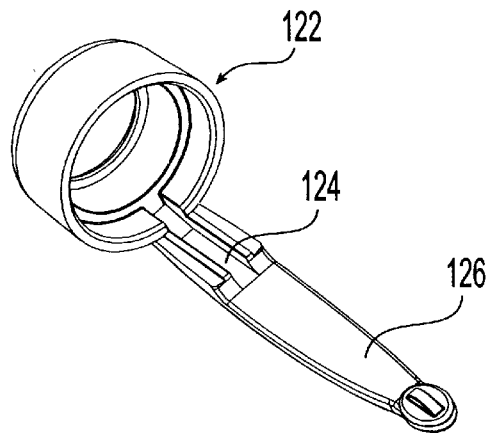
FIG. 18 is a perspective view of a button cap.

A distal end of distal housing 88 has crush ribs 120 for providing an interference fit with a button cap 122 (FIG. 18). A slot 124 in a clip 126 of button cap 122 slides into ridge 128 of distal housing 88. Clip 126 functions like a pen clip and provides a convenient way to attach injector 10 to an article of clothing, a clipboard, etc. Clip 126 can also be used for leverage when rotating distal housing 88 with respect to proximal housing 86 for arming and dosing.

Figure 19:
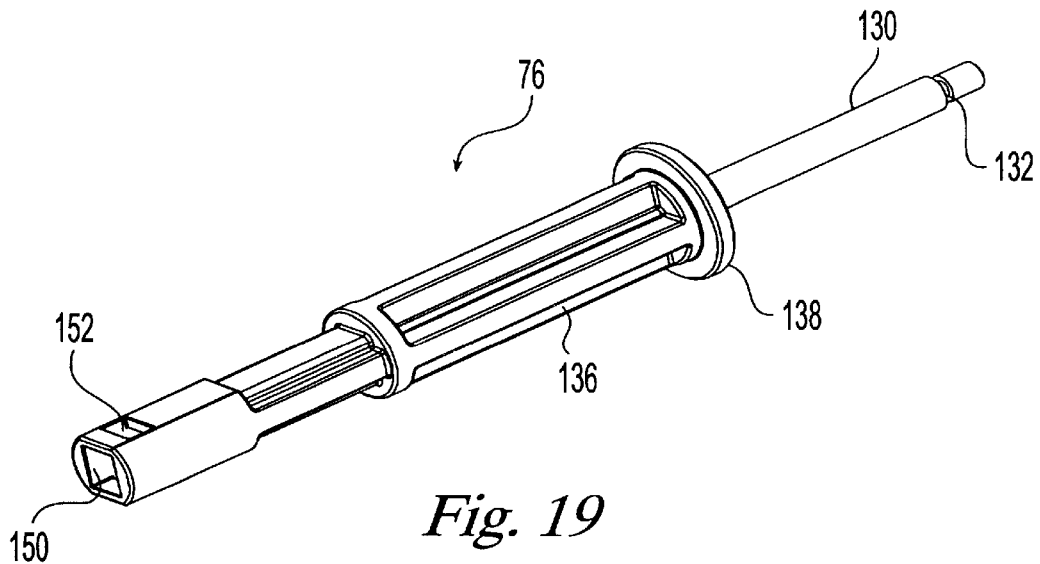
FIG. 19 is a perspective view of a ram.
Figure 20:
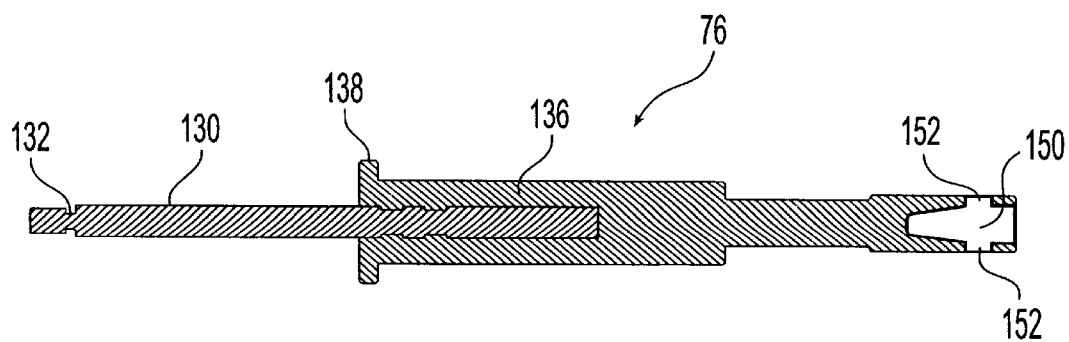
FIG. 20 is a cross-sectional view of the ram of FIG. 19.
Figure 21:
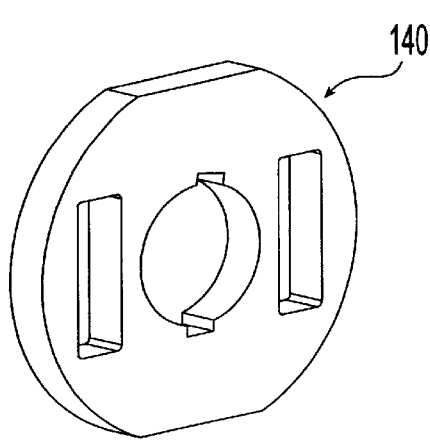
FIG. 21 is a perspective view of ram retainer.

As previously noted, plunger 62 is connected to ram 76. This connection forms when needle free syringe assembly 14 is coupled to power pack assembly 16. Specifically, as nozzle member 60 is inserted in proximal housing 86, a proximal end 130 of ram 76 (FIGS. 19 and 20) pushes against plunger 62 to move plunger 62 out of the expanded area of tail 68 so that legs 74 compress around ring 132 to connect plunger 62 to ram 76. Ram 76 is in turn operatively associated with an energy source 134 for moving ram 76 and plunger 62 to force medicament out of orifice 69 of nozzle member 60. Energy source 134 can be a coil spring, a gas spring, or a gas propellant. Ram 76 has a central body 136 that terminates in a disk 138. Disk 138 cooperates with a ram retainer 140, shown in FIGS. 1 and 21, to limit the distance that ram 76 can travel toward nozzle member 60. One important safety aspect of this feature is that ram 76 cannot become a dangerous projectile if injector assembly 10 is fired when needle free syringe assembly 14 is not present.

Figure 22:
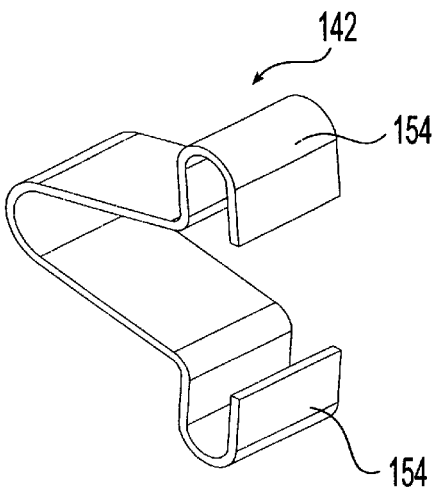
FIG. 22 is a perspective view of a latch spring.
Figure 23:
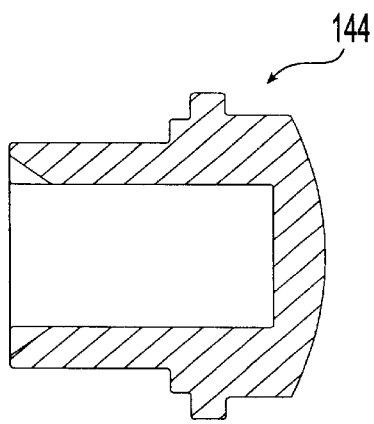
FIG. 23 is a cross-sectional view of a button.
Figure 24:
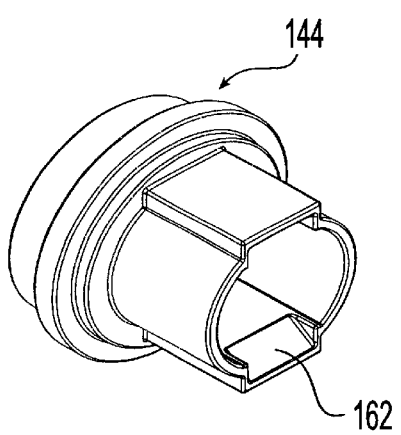
FIG. 24 is a perspective view of the button of FIG. 23.
Figure 25:
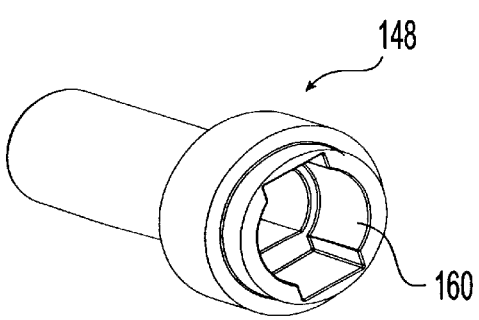
FIG. 25 is a perspective view of a latch housing.
Figure 26:
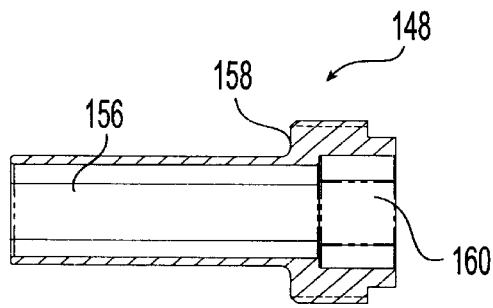
FIG. 26 is a cross-sectional view of the latch housing of FIG. 25.
Figure 27:
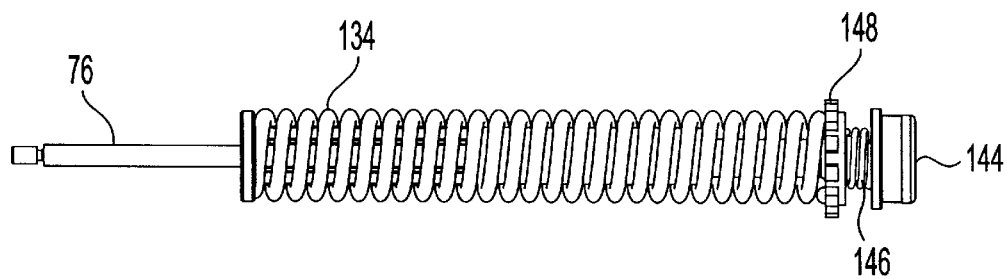
FIG. 27 is a perspective view of another embodiment of a trigger assembly.
Figure 28:
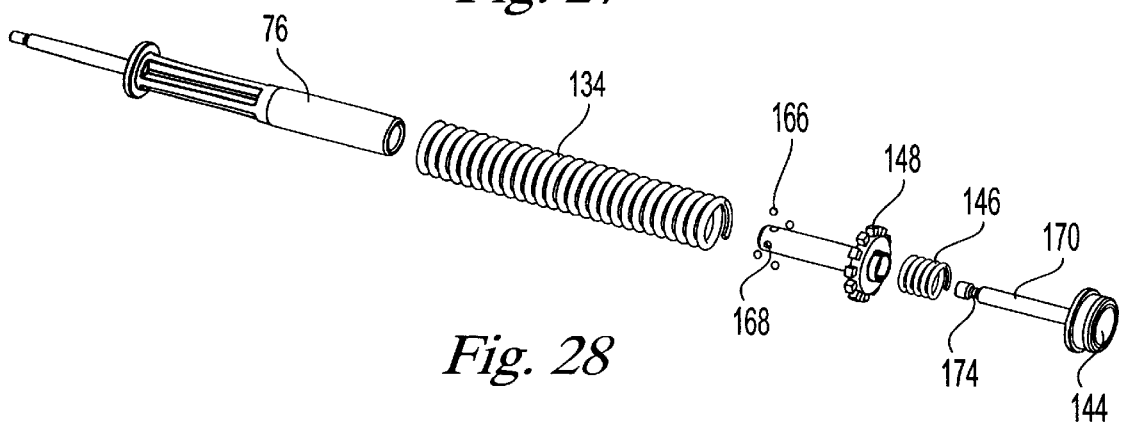
FIG. 28 is an exploded perspective view of the trigger assembly of FIG. 27.

Medical injector 10 includes a trigger assembly for firing power pack assembly 16. Two exemplary embodiments of a trigger assembly are now described. In the first, the trigger assembly includes a latch spring 142 (FIG. 22) for holding energy source 134 until firing, a button 144 (FIGS. 23 and 24) for firing medical injector 10, a button return spring 146 (FIGS. 1 and 8) for biasing button 144 outward, a latch housing 148 (FIGS. 25 and 26) which cooperates with latch spring 142 and button 144 to allow ram 76 to move upon firing, and button cap 122 (FIG. 18) for holding the trigger assembly in place. The distal end of ram 76 has a cavity 150 for receiving latch spring 142. Cavity 150 has a pair of notches 152 out of which U-shaped ends 154 of latch spring 142 can protrude when latch spring 142 is not compressed. After medical injector 10 is fired, ram 76 has traveled proximally through distal housing 88 so that cavity 150 is positioned within a bore 156 of latch housing 148. Because of the size of bore 156 compared to latch spring 142, latch spring 142 is compressed so that all of latch spring 142 is contained in cavity 150 when latch spring 142 is within bore 156. In other words, U-shaped ends 154 do not protrude through notches 152 when latch spring 142 is within bore 156. In order to re-arm medical injector 10, distal housing 88 is rotated clockwise with respect to proximal housing 86. This rotation compresses energy source 134 between a ridge 158 of latch housing 148 and disk 138 of ram 76. As distal housing 88 moves proximally toward proximal housing 86, latch housing 148 also moves proximally until cavity 150 of ram 76 is located within an expanded keyed area 160. When notches 152 of cavity 150 reach keyed area 160, U-shaped ends 154 of latch spring 142 expand to retain latch spring 142 to keyed area 160 and thereby keep energy source 134 compressed. In order to release latch spring 142 from keyed area 160, button 144 must be depressed. Depressing button 144 causes ramped surfaces 162 to move proximally and thereby compress latch spring 142 to disengage U-shaped ends 154 from keyed area 160.

Figure 29:
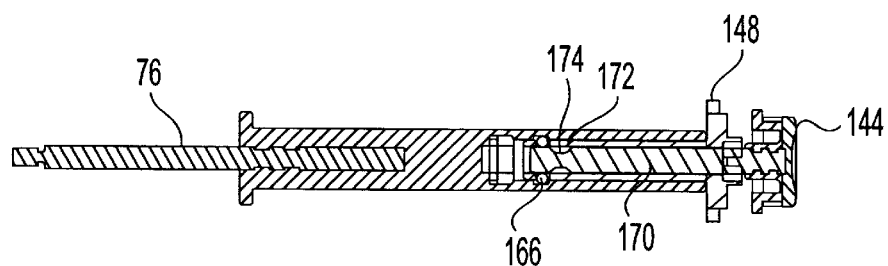
FIG. 29 is a cross-sectional view of the trigger assembly of FIG. 27 in the latched position with the energy source and button return spring removed.

FIGS. 27–30 show the second exemplary embodiment of a trigger assembly. When the components are assembled, the position of latch housing 148 is fixed, energy source 134 is trying to push ram 76 away from latch housing 148, and button return spring 146 is trying to push button 144 from latch housing 148. When ram 76 compresses energy source 134, an internal groove 164 of increased diameter of ram 76 lines up with latch balls 166 and holes 168 in latch housing 148. This allows button return spring 146 to move button 144 away from latch housing which forces latch balls 166 into internal groove 164 of ram 76. This movement is possible because a stem 170 of button 144 has a tapering surface 172 leading to an area 174 of decreased diameter (in comparison to the rest of stem 170). Latch balls 166 are now captured in latch housing 148 and hold ram 76 in place. This is referred to as the latched position and is best seen in FIG. 29.

Figure 30:
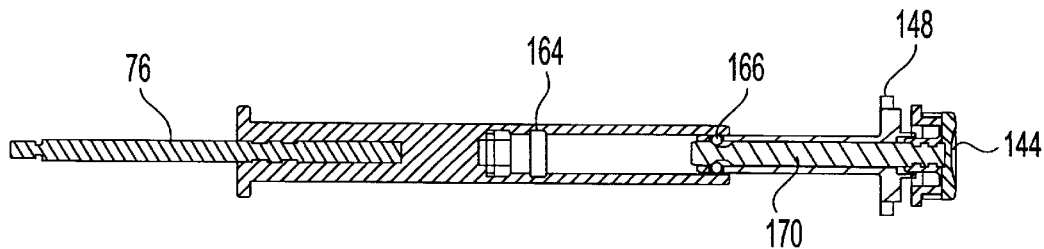
FIG. 30 is a cross-sectional view of the trigger assembly of FIG. 27 in the fired position with the energy source and button return spring removed.

When button 144 is depressed, area 174 on stem 170 of button 144 lines up with holes 168 in latch housing 148. This allows energy source 134 to force ram 76 away from latch housing 148, thereby pushing latch balls 166 into area 174 on stem 170. This is referred to as the fired position and is best seen in FIG. 30. As is evident from FIGS. 29 and 30, latch balls 166 are always contained between ram 76, latch housing 148, and button 144. This arrangement minimizes the possibility that latch balls 166 become dislodged and increases the reliability of the trigger assembly.

The operation of medical injector 10 will now be described, with a just-fired injector as the starting point and with reference to the first-described trigger assembly. In order to re-arm injector 10, the user rotates distal housing 88 clockwise with respect to proximal housing 86 to compress energy source 134 between ridge 158 of latch housing 148 and disk 138 of ram 76. The rotation continues until latch spring 142 is retained within keyed area 160 to thereby keep energy source 134 compressed. Medicament is drawn into fluid chamber 64 by counterclockwise rotation of distal housing 88 with respect to proximal housing 86, thus aspirating the fluid. Specifically, the rotation causes distal movement of ram 76 and plunger 62 (because ram 76 is locked to distal housing 88), which in turn creates a vacuum in fluid chamber 64 to draw medicament through medicament cartridge 18 and adapter 20 and into fluid chamber 64. In order to fire injector 10, cartridge assembly 12 is removed from needle free assembly 14 and the proximal end of needle free syringe assembly 14 is placed against the skin at the desired injection site. Button 144 is depressed to disengage latch spring 142 from keyed area 160. This allows energy source 134 to return to its uncompressed state and move ram 76 and plunger 62 proximally so that medicament is ejected through orifice 69 at a pressure sufficient to jet inject the medicament.

As is evident from the description of the structure and operation of medical injector 10, injector 10 is a compact injector that is convenient to transport. Injector 10 is also simple to use and operate. In particular, injector 10 is ready to be loaded every time cartridge assembly 12 is placed on needle free syringe assembly 14.

Figure 31:
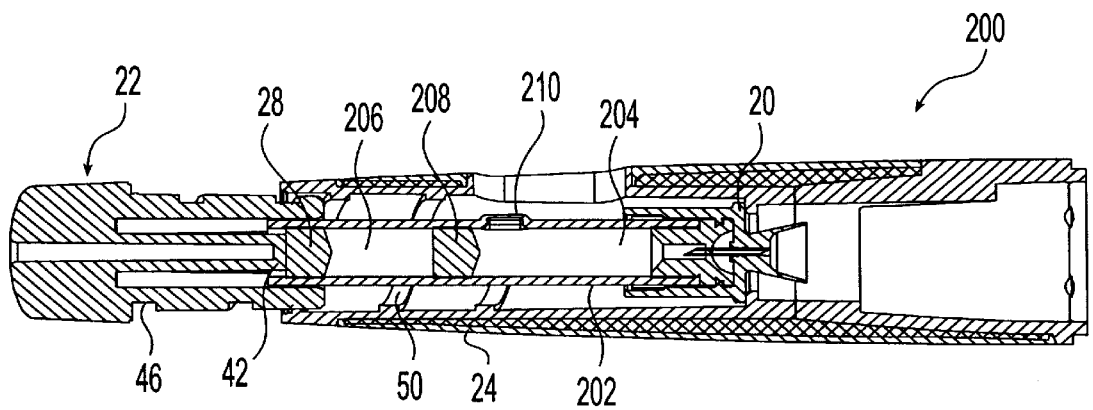
FIG. 31 is a cross-sectional view of another embodiment of a cartridge assembly for lyophilized medicament prior to reconstitution.
Figure 32:
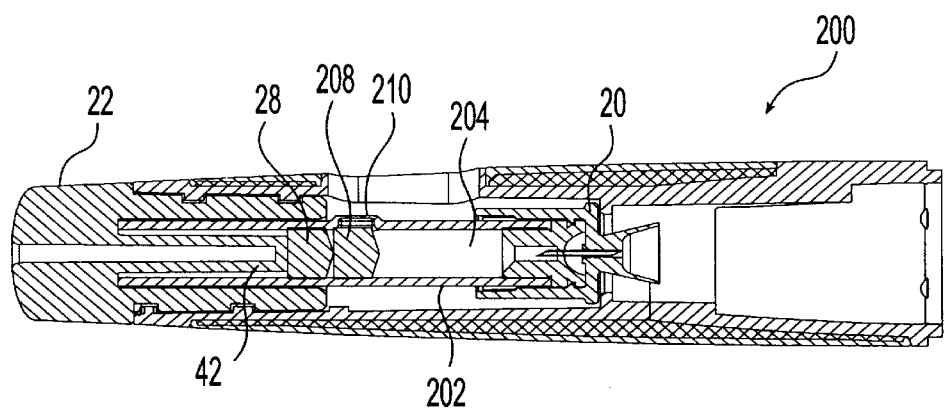
FIG. 32 is a cross-section view of the cartridge assembly of FIG. 27 after the lyophilized medicament has been reconstituted.

The three assembly (cartridge, needle free syringe, and power pack) design allows an individual assembly to be modified without affected the other two assemblies. For example, FIGS. 31 and 32 show another embodiment of a cartridge assembly 200 that is used for lyophilized medicaments that are reconstituted just prior to use. A lyophilized medicament cartridge 202 has a first chamber 204 that contains the lyophilized medicament, a second chamber 206 that contains the reconstituting fluid, and a dividing stopper 208 separating the two. Medicament cartridge 202 also has a bypass 210 so that once dividing stopper 208 reaches bypass 210, the reconstituting fluid can enter first chamber 204 to reconstitute the lyophilized medicament. Movement of dividing stopper results from the threading of cap 22 to cartridge housing 24, with threads 46, 50. Specifically, as cap 22 is threaded onto cartridge housing 24, post 42 pushes stopper 28 towards adapter 20. The resulting fluid pressure of reconstituting fluid causes dividing stopper 208 to also move toward adapter 20 until bypass 210 is reached. Once dividing stopper 208 reaches bypass 210, further movement of stopper 28 allows the reconstituting fluid to enter into first chamber 204 and reconstitute the lyophilized medicament.

Figure 33:
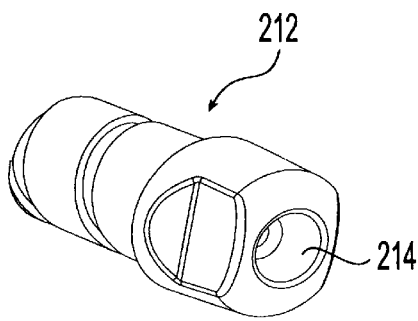
FIG. 33 is a perspective view of another embodiment of a cap according to the present invention.
Figure 34:
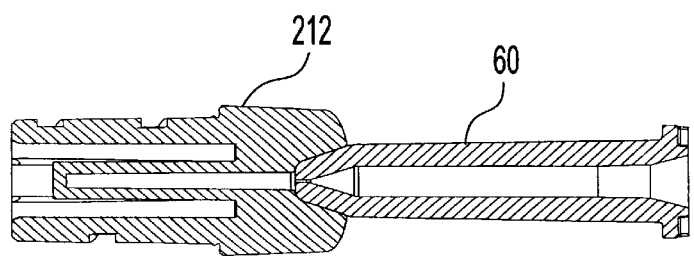
FIG. 34 is a cross-sectional view of the cap of FIG. 29 with a needle free syringe assembly.

FIG. 33 shows another embodiment of a cap 212 with a bore 214 having a shape and size that matches that of the proximal end of nozzle member 60 of needle free syringe assembly 14. As shown in FIG. 34, the proximal end of nozzle member 60 fits snugly into bore 214. Because of the tight fit, cap 212 and nozzle member 60 rotate together. Thus, cap 212 can be used to attach or detach nozzle member 60 from needle free syringe assembly 14.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. A medical injector assembly, comprising:
    a syringe assembly comprising:
        a nozzle member defining a fluid chamber and having a proximal end configured and dimensioned for mating with the second side of the adapter and a distal end; and
        a plunger movable in the fluid chamber;
    a power pack assembly comprising:
        a housing having a proximal end connectable with the distal end of the nozzle member and a distal end;
        a trigger assembly comprising:
            a ram having proximal and distal ends and a bore, the proximal end coupled to the plunger and the bore having a cavity,
            a latch housing having a tubular body with a channel, at least a portion of the body insertable in the bore of the ram,
            a plurality of latch holes located on the body of the latch housing, each of the plurality of latch holes having associated therewith a latch ball, and
            a button having a stem with proximal and distal ends and a groove located near the distal end, at least a portion of the stem is insertable in the channel of the latch housing,
            wherein in a latched position each latch ball is captured in the cavity of the ram bore to thereby prevent the energy source from moving the plunger in the first direction and in a fired position the groove of the button stem aligns with the plurality of latch holes and latch balls to release the latch balls from the cavity of the ram bore and thereby activate the energy source to move the plunger in the first direction; and
        an energy source operatively associated with the trigger assembly so that movement of the trigger assembly activates the energy source to move the plunger in a first direction to expel medicament from the fluid chamber.

2. The medical injector of claim 1, further comprising:
    a cartridge assembly for holding a medicament cartridge with a chamber containing medicament, a first end of the chamber having a seal, and a second end of the chamber having a stopper movable towards the seal as medicament is drawn out of the chamber, the cartridge assembly comprising:
        an adapter with a first side configured and dimensioned to mate with the first end of the chamber and having a needle for penetrating the seal upon insertion of the cartridge assembly in the adapter, a second side, and a wall therebetween, the wall having an opening in fluid communication with the needle to create a pathway for medicament as medicament is drawn out of the chamber,
        a cap and cartridge housing with an interior for receiving the second end of the chamber and an end having a post causing movement of the stopper toward the seal as the medicament cartridge is inserted in the interior to thereby eliminate adhesion between the chamber and the stopper, and
        a housing having a first end connectable with the cap and a second end connectable with the adapter.

3. The medical injector of claim 2, wherein the energy source and the trigger are associated to move the plunger in the first direction to expel the medicament from the fluid chamber when the cartridge assembly is not connected to the syringe assembly.

4. The medical injector of claim 3, wherein movement of the plunger in a second direction draws medicament out of the cartridge chamber and into the fluid chamber when the cartridge assembly is connected to the syringe assembly.

5. The medical injector of claim 1, wherein the syringe assembly comprises a needle free syringe assembly.

6. An injecting device, comprising:
    the medical injector assembly of claim 1; and
    a filling assembly that comprises:
        a cartridge housing configured for receiving a first end of a cartridge that has a chamber containing a medicament and first and second ends, the first end including a seal for sealing the medicament in the chamber, and the second end including a stopper sealingly disposed in the chamber;
        an adapter associated with the cartridge housing and configured for coupling the chamber to the syringe assembly for transferring the medicament to the fluid chamber; and
        a post associated with the cartridge housing in a post position from which movement towards the adapter is substantially prevented, wherein the post is configured such that positioning of the second end of the cartridge in a first position with respect to the post and of the post in the post position causes the post to displace the stopper towards the seal by an amount sufficient to reduce or eliminate adhesion between the chamber and the stopper for permitting filling of the fluid chamber from the chamber and for substantially preventing said movement of the cartridge past the first position.

7. The injecting device of claim 6, wherein the post is configured such that movement to the first position is insufficient to expel a substantial amount of the medicament from the chamber with the seal opened by the opening member.

8. The injecting device of claim 6, further comprising a cap having an engaged association with the cartridge housing in an engaged position from which movement therebetween past the engaged position towards the adapter is substantially prevented, wherein the post extends from the cap in the post position and the cap is configured for substantially preventing said movement of the cartridge past the first position.

9. The injecting device of claim 8, wherein the cap is configured and dimensioned for receiving the second end of the cartridge such that movement of the second end into the cap causes the post to displace the stopper towards the seal by said amount sufficient to reduce or eliminate adhesion between the chamber and the stopper.

10. The injecting device of claim 8, wherein the cap and the adapter housing are configured such that the engagement thereof causes sufficient displacement of the stopper for purging an amount of any air contained in the cartridge with the seal opened prior to the attachment to the syringe assembly.

11. The injecting device of claim 6, wherein the post is disposed and configured such that the engagement of the cap with the adapter housing causes the post to move the seal to the first position.

12. The injecting device of claim 6, wherein the adapter comprises a cartridge opening member configured for opening the seal to permit extraction of the medicament therefrom.

13. The injecting device of claim 12, wherein the adapter comprises a needle disposed and configured for penetrating the seal for said opening of the seal.

14. The injecting device of claim 6, wherein the adapter comprises a wall that defines a wall opening in fluid communication with the cartridge opening member to create a pathway for drawing the medicament out of the chamber.

15. The injecting device of claim 6, wherein the adapter is configured for connecting the cartridge to the syringe assembly to allow the medicament to flow from the chamber into the fluid chamber.

16. The injecting device of claim 6, wherein the adapter is configured for engaging the first end of the cartridge.

17. The injecting device of claim 16, wherein the adapter comprises a frangible retaining member configured for engaging and retaining the first end of the cartridge and for breaking upon removal of the cartridge from the adapter housing for inhibiting repeat uses of the filling assembly.

18. The injecting device of claim 17, wherein the frangible retaining member comprised a plurality of resilient tabs configured for flexing outward upon insertion of the medicament cartridge into the adapter and flexing inward about the first end of the cartridge to engage and retain the cartridge.

19. The injecting device of claim 6, wherein the post is associated with the cartridge housing in the post position for allowing the medicament to be aspirated from the chamber into the fluid chamber.

20. The injecting device of claim 6, wherein the housing defines a window for viewing at least a portion of the medicament cartridge.

21. The injecting device of claim 6, further comprising the cartridge.

22. The injecting device of claim 21, wherein the medicament chamber comprises a first chamber containing a lyophilized medicament, a second chamber containing a reconstituting fluid, a dividing member separating the first and second chambers, and a bypass channel for providing fluid communication between the first and second chambers upon movement of the dividing member, wherein fluid pressure generated by movement of the stopper causes movement of the dividing member.

23. The injecting device of claim 1, wherein the syringe assembly and filling assembly comprise threaded portions configured for connecting to each other.

24. A medical injector assembly, comprising:
a needle free syringe assembly comprising:
a nozzle member defining a fluid chamber and having a proximal end configured and dimensioned for mating with the second side of the adapter and a distal end; and
a plunger movable in the fluid chamber; and
a power pack assembly comprising:
a housing having a proximal end connectable with the distal end of the nozzle member and a distal end;
a trigger assembly comprising:
a ram having a proximal end coupled to the plunger and a distal end with a cavity,
a latch housing connected to the power pack assembly and having a body with a bore leading to a keyed opening, the bore and keyed opening configured and dimensioned for receiving at least a portion of the ram, and
a latch spring located in the ram cavity and having first and second U-shaped ends, wherein the U-shaped ends extend through cutouts located in the ram when the latch spring is located in the keyed opening to thereby prevent the energy source from moving the plunger in the first direction and the U-shaped ends compress within the ram cavity when the latch spring is located in the bore to thereby allow the energy source to move the plunger in the first direction; and
an energy source operatively associated with the trigger assembly so that movement of the trigger assembly activates the energy source to move the plunger in a first direction to expel medicament from the fluid chamber when the cartridge assembly is not connected to the needle free syringe assembly and movement of the plunger in a second direction draws medicament out of the cartridge chamber and into the fluid chamber when the cartridge assembly is connected to the needle free syringe assembly.

25. The medical injector assembly of claim 24, further comprising a cartridge assembly for holding a medicament cartridge with a chamber containing medicament, a first end of the chamber having a seal, and a second end of the chamber having a stopper movable towards the seal as medicament is drawn out of the chamber, the cartridge assembly comprising:
an adapter with a first side configured and dimensioned to mate with the first end of the chamber and having a needle for penetrating the seal upon insertion of the cartridge assembly in the adapter, a second side, and a wall therebetween, the wall having an opening in fluid communication with the needle to create a pathway for medicament as medicament is drawn out of the chamber;
a cap with an interior for receiving the second end of the chamber and an end having a post causing movement of the stopper toward the seal as the medicament cartridge is inserted in the cap to thereby eliminate adhesion between the chamber and the stopper; and
a housing having a first end connectable with the cap and a second end connectable with the adapter.

* * * * *